United States Patent [19]
Forster et al.

[11] Patent Number: 5,152,914
[45] Date of Patent: Oct. 6, 1992

[54] SHAMPOO COMPOSITION

[75] Inventors: Deborah J. Forster, Leeds; David A. Hitchen, Cheshire; Euan S. Reid, Wirral, all of United Kingdom

[73] Assignee: Chesebrough-Pond's USA Co., Division of Conopco, Inc., Greenwich, Conn.

[21] Appl. No.: 529,978

[22] Filed: May 29, 1990

[30] Foreign Application Priority Data

May 30, 1990 [GB] United Kingdom ............... 8912391

[51] Int. Cl.$^5$ .................... C11D 17/00; A61K 7/06
[52] U.S. Cl. ........................ 252/174; 252/174.15; 252/174.23; 252/DIG. 1; 252/DIG. 13; 424/70
[58] Field of Search ............. 252/173, 174.23, 174.15, 252/DIG. 1, DIG. 13; 424/70

[56] References Cited

U.S. PATENT DOCUMENTS

| 3,957,970 | 5/1976 | Korkie | 252/DIG. 13 |
| 3,964,500 | 6/1976 | Drakoff | 252/DIG. 13 |
| 4,364,837 | 12/1982 | Pader | 252/DIG. 13 |
| 5,063,052 | 11/1991 | Grollier et al. | 252/78.3 |

FOREIGN PATENT DOCUMENTS 0074264 3/1983 European Pat. Off.
0181773 5/1986 European Pat. Off.

OTHER PUBLICATIONS

European Search Report and Annex.
H. Janistyn, Handbuch der Kosmetika und Riechstoffe, "Die Kosmetischen Grundstoffe", vol. i, 1978, Dr. Alfred Huthig Verlag, pp. 732–738; pp. 836–840 (No translation).

Primary Examiner—A. Lionel Clingman
Assistant Examiner—William S. Parks
Attorney, Agent, or Firm—Milton L. Honig

[57] ABSTRACT

A shampoo composition comprising in addition to water
(a) from 2 to 40% by weight of surfactant chosen from anionic, nonionic or amphoteric surfactants, or mixtures thereof;
(b) from 0.01 to 10% by weight of insoluble, non-volatile silicone;
(c) from 0.5 to 5% by weight of suspending agent chosen from polyethylene glycol mono- or diesters of $C_{16-22}$ fatty acid, having from 2 to 7 ethylene oxide groups.

The composition may further comprise a cationic conditioning agent.

10 Claims, No Drawings

SHAMPOO COMPOSITION

BACKGROUND OF THE INVENTION

The present invention relates to shampoo compositions, and more particularly to shampoo compositions containing non-volatile silicone materials which condition the hair leaving it softer and more manageable.

When washing the hair with conventional shampoo compositions, the natural oils are removed together with the dirt and unwanted oils. When too much of the natural oil is removed, for example by especially frequent washing, the hair becomes less easy to comb or style, and subject to static build-up causing "flyaway".

Hair conditioners have been developed to try to restore the condition of the hair. These compositions are normally applied to the hair after shampooing, left on the hair for a period of time and rinsed off. This process is time consuming and expensive since two separate products are needed.

Conditioning shampoos containing cationic conditioning agents have been disclosed for example in EP 18 717 (Unilever). These cationic agents confer some conditioning benefit on the hair, but are often thought to leave a residue on the hair, which may cause dulling on dry hair.

Silicone oils are known to be conditioning agents and their use in conditioning shampoos has been proposed for example in EP 74 264 (Unilever) and EP 77 920 (Kao). However, it has been found that care is needed when formulating silicone containing shampoos as the compositions are often unstable and the silicone oil tends to separate out.

EP 181 773 (Procter & Gamble) attempts to solve the problem of stability by incorporating e.g. ethylene glycol mono or di-stearates into the shampoo composition to act as a suspending agent for the silicone oil. In order to act as a suspending agent, crystals of the ethylene glycol stearate have to form in the surfactant, and this is achieved by heating the mixture to the point at which the ethylene glycol stearate dissolves in the surfactant. This process is relatively expensive as well as time consuming, since the mixture must be allowed to cool before further processing can take place.

We have found that suspension of silicone oils in a shampoo composition can be achieved more efficiently and at a lower cost by use of certain specific suspension agents.

The invention accordingly provides an aqueous shampoo composition comprising in addition to water
(a) from 2 to 40% by weight of surfactant chosen from anionic, nonionic or amphoteric surfactant, or mixtures thereof;
(b) from 0.01 to 10% by weight of insoluble, non-volatile silicone;
(c) from 0.5 to 5% by weight of suspending agent chosen from polyethylene glycol mono- or diesters of $C_{16-22}$ fatty acid having from 2 to 7 ethylene oxide groups.

DETAILED DESCRIPTION OF THE INVENTION

(a) Surfactant

The composition according to the invention comprises a surfactant chosen from anionic, nonionic or amphoteric surfactant or mixtures thereof.

Suitable anionic surfactants are the alkyl sulphates, alkyl ether sulphates, alkaryl sulphonates, alkyl succinates, alkyl sulphosuccinates, N-alkoyl sarcosinates, and alpha-olefin sulphonates, especially their sodium, magnesium, ammonium and mono-, di- and triethanolamine salts. The alkyl groups generally contain from 8 to 18 carbon atoms and may be unsaturated. The alkyl ether sulphates may contain from one to 10 ethylene oxide or propylene oxide units per molecule, and preferably contain 2 to 3 ethylene oxide units per molecule.

Examples of suitable anionic surfactants include sodium lauryl sulphate, sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, sodium lauryl ether sulphate 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$-$C_{18}$) primary or secondary linear or branched chain alcohols or phenols with alkylene oxides, usually ethylene oxide and generally 6-30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates and alkyl carboxyglycinates, wherein the alkyl groups have from 8 to 18 carbon atoms. Examples include lauryl amine oxide, cocamidopropyl betaine, cocodimethyl sulphopropyl betaine and preferably cocobetaine.

The surfactants are present in the shampoo composition of the invention in an amount of from 2 to 40% by weight, and preferably from 5 to 30% by weight.

If an amount of less than 2% by weight of surfactant is present in the composition, inadequate foaming is achieved, and if more than 40% by weight is present, no further increase in cleansing power or foaming ability is observed.

(b) Silicone

The shampoo composition of the invention also comprises an insoluble, non-volatile silicone, which may be a polyalkyl siloxane, a polyalkylaryl siloxane, or mixtures thereof. The silicone should be insoluble in the matrix of the shampoo.

Suitable polyalkyl siloxanes include polydimethyl siloxanes having a viscosity of from 5 to 100,000 centistokes at 25° C. These siloxanes are available commercially from the General Electric Company as the Viscasil series and from Dow Corning as the DC 200 series. The viscosity can be measured by means of a glass capillary viscometer as set forth in Dow Corning Corporate Test Method CTM0004 Jul. 20, 1970.

Also suitable is polydiethyl siloxane.

The polyalkylaryl siloxanes which may be used in the shampoo compositions of the invention include polymethylphenyl polysiloxanes having a viscosity of from 15 to 65 centistokes at 25° C. These siloxanes are available commercially from the General Electric Company as SF 1075 methyl phenyl fluid or from Dow Corning as 556 Cosmetic Grade Fluid.

Also suitable are silicone gums, such as those described in U.S. Pat. No. 4 152 416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000, and specific examples include polydimethyl siloxane copolymer, polydimethyl siloxane/diphenyl/methylvinylsiloxane copolymer, polydimethylsiloxane/methylvinylsiloxane copolymer and mixtures thereof.

Further examples of insoluble, non-volatile silicones suitable for use in the compositions of the invention are the polyaminofunctional silicones such as DC 929, available from Dow Corning.

By polyaminofunctional silicone is meant polyalkyl or polyalkylaryl siloxane in which the silicone chain is at least partly substituted by $-NRR^1$ wherein R and $R^1$ are the same or different and are H, alkyl or phenyl.

The siloxanes described above may be incorporated directly into the shampoos of the invention or may be added as a preformed emulsion, such as BY22-007 and BY22-026 available from Toray Silicone Co. Limited.

The shampoo compositions of the invention contain from 0.01 to 10% by weight, preferably from 0.5 to 5% by weight, of insoluble, non-volatile silicone. If less than 0.01% by weight is present in the composition, little conditioning benefit is observed, and if more than 10% by weight is present, the hair will appear greasy.

(c) Suspending agent

The suspending agent used in the shampoo composition of the invention is chosen from polyethylene glycol mono- or di-esters of $C_{16-22}$ fatty acids having from 2 to 7 ethylene oxide groups. Suitable esters are the stearates, oleates, behenates or myristates, preferably the distearates.

The most preferred ester is polyethylene glycol distearate having 3 ethylene oxide groups. This material is available commercially, for example, from Henkel in the pearliser concentrate Euperlan PK 900, or as the solid Genapol TS from Hoechst.

Crystals of the suspending agent may have a thin platelet shape, and when these crystals are dispersed in the shampoo of the invention, they can help to suspend dispersed particles or droplets by so-called "hindered settling". This also contributes to the pearlescent effect often observed with such suspending agents.

Suspending agents must therefore have the following characteristics (a) they must have higher dissolution and melting points than normal shampoo storage temperatures (if the crystals dissolve or melt, then the suspending ability is lost);

(b) they must form thin, platelet-type crystals in the shampoo.

Monomeric ethylene glycol mono- and di-stearates have been used to suspend particles (eg. EP 18 1 773 and EP 34846, both Procter & Gamble). In order to make these shampoos it is necessary to heat the mixture of suspending agent (A) and surfactant (B) to above the melting/dissolution point of (A) in (B), and then slowly cool the resultant emulsion whereby platelets of suspending agent form.

Polyethylene glycol (3) distearate (available as Genapol TS from Hoechst) has a melting point of 50° C. and a freezing point of 42.1° C., whereas ethylene glycol distearate (available as Radia 7267 from Oleofina) has a melting point of 64.2° C. and a freezing point of 59.8° C.

Other suitable suspending agents include polyethylene glycol (3) dipalmitate (available as Nikkol Pearl-3216) and polyethylene glycol (4) dioleate (available as Kessco PEG200 dioleate from Akzo).

The polyethylene glycol ester suspending agents used in the shampoos of the invention have lower melting and freezing points and can therefore be more easily processed giving significant savings in time and energy.

The suspending agents are present in the shampoo compositions of the invention in amounts of from 0.5 to 5% by weight. If less than 0.5% by weight is used in the composition, separation will take place, and the silicone will rise to the top, and if more than 5% by weight is used, the shampoo will be thick and difficult to pour.

CATIONIC CONDITIONING AGENT

The shampoo composition of the invention may also further comprise a cationic conditioning agent.

Suitable cationic conditioning agents include the cationic cellulose ethers described in U.S. Pat. Nos. 3 816 616 and 4 272 515 and which are available commercially from Union Carbide Corporation as Polymer JR. Other suitable materials are the cationic polygalactomannan gum derivatives describes in U.S. Pat. No. 4 298 494 which are commercially available under the trade mark Jaguar from Celanese-Stein Hall. An example of a suitable material has the CTFA designation guar hydroxypropyltrimonium chloride and is available under the the name Jaguar C13S, which has a degree of substitution of the cationic groups of about 0.13. Other suitable materials include that known as Jaguar C17 (degree of substitution of about 0.25 to 0.31), and Jaguar C16 which is hydroxypropylated cationic guar derivative containing hydroxypropyl substituent groups as well as cationic quaternary ammonium groups. In Jaguar C16, the degree of substitution is 0.11 to 0.16 and the moles of substitution of hydroxypropyl groups is 0.8 to 1.1.

Other cationic conditioning agents useful in the shampoos of the present invention include cationic polyamide polymers such as the low molecular weight adipic acid/diethylene-triamine polyamide and the copolymers of vinylpyrrolidone and dimethylaminoethyl methacrylate quaternised with dimethyl sulphate (Gafquat 755, GAF Corporation) described in U.S. Pat. No. 4 080 310; the graft cationic copolymer containing N-vinylpyrrolidone, dimethyaminoethyl methacrylate and polyethylene glycol described in U.S. Pat. No. 4 048 301; the mineral acid salts of the amino alkyl esters of homo- and copolymers of unsaturated carboxylic acids having from 3 to 5 carbon atoms described in U.S. Pat. No. 4 009 256; and the polymers of etherified starch described in U.S. Pat. No. 3 186 911.

The high molecular weight polymers sold under the trade mark Merquat by Merck & Co. Inc., are cationic polymers which are also suitable for use in the present shampoos. Representative ones are Merquat 100, a highly charged cationic dimethyldiallylammonium chloride homopolymer, and Merquat 550, a highly charged cationic copolymer prepared with dimethyldiallylammonium chloride and acrylamide. These materials are designated in the CFTA dictionary as Quaternium-40 and Quaternium-41, respectively.

Cationic surfactants such as mono-, di- and tri-alkyl quaternary ammonium salts may also be used as the cationic conditioning agent in the shampoos of the invention. Suitable examples are cetyl trimethylammonium chloride, cetyl trimethylammonium bromide and stearyltrimethylammonium chloride.

The cationic conditioning agent is preferably present in the shampoo composition of the invention in an amount of from 0.1 to 5% by weight, most preferably in an amount of from 0.2 to 3% by weight.

OTHER INGREDIENTS

The shampoo of the invention may also include minor amounts of other ingredients such as antibacterial agents, foam boosters, pearlescers, perfumes, dyes, colouring agents, preservatives, thickeners, proteins, polymers, phosphate esters and buffering agents.

EXAMPLES

The following Examples illustrate the invention.

| Example 1 | % wt |
|---|---|
| Sodium lauryl ether sulphate (2EO) | 13 |
| Cocamidopropyl betaine | 2.3 |
| Euperlan PK 900 | 10 (1) |
| Silicone emulsion | 5 (2) |
| Jaguar C13S | 0.4 |
| preservative, colour, perfume | |
| Water | to 100 |

(1) Euperlan PK 900 comprises
20% wt polyethylene glycol (3EO) distearate
13% wt sodium lauryl ether sulphate (2EO)
(2) Silicone emulsion
The silicone emulsion used in Example 1 comprises

| | |
|---|---|
| SLES 2EO (25% a.d.) | 46.0 |
| Cetostearyl alcohol | 4.0 |
| Silicone oil (DC 200, viscosity 60.000 cS) | 50.0 |
| preservative | |

The silicone oil and cetostearyl alcohol were heated to 75° C. and mixed with a paddle stirrer, in the main vessel.

SLES 2EO was heated to 70° C. and added to the main vessel. Mixing was continued for 15 minutes. The mixture was cooled to 30° C. and preservative was added.

| Example 2 | wt % |
|---|---|
| Ammonium lauryl sulphate (ALS) | 12.0 |
| Coco Amidopropyl Betaine | 2.0 |
| Coco Diethanolamide | 1.0 |
| Silicone Oil (DC 200-60,000 cS) | 2.0 |
| Jaguar C13S | 0.3 |
| Genapol TS | 2.0 |
| Preservative, Colour, Perfume | qs |
| Water | to 100 |

This is prepared by hot mixing (55° C.) the silicone oil and Genapol TS with a 25% wt ALS solution using a high shear mixer eg. Silverson. This mixture is then allowed to cool and mixed with the remaining ingredients using a paddle stirrer.

| Example 3 | wt % |
|---|---|
| Sodium lauryl ether sulfate (2EO) | 14.0 |
| Coco Betaine | 2.0 |
| Silicone Emulsion | 4.0 (3) |
| polymer JR 400 | 0.5 |
| Euperlan PK 900 | 10.0 |
| Preservative, Colour, Perfume | qs |
| Water | to 100 |
| (3) Silicone emulsion comprises | |
| Lauryl Alcohol Ethoxylate 2EO | 2.0 |
| Lauryl Alcohol Ethoxylate 21EO | 2.0 |
| Silicone Oil (60,000 cS) | 50.0 |

| Example 3 -continued | wt % |
|---|---|
| Preservative | qs |
| Water | to 100 |

This emulsion is prepared by hot mixing (70° C.) all the ingredients using a high sheer mixer (homomixer) and then cooling.

The shampoo is prepared using a simple cold process whereby all the ingredients are mixed using a paddle stirrer.

| Example 4 | % wt |
|---|---|
| Sodium lauryl ether sulphate 2EO | 12.0 |
| Coconut diethanolamide | 2.5 |
| Jaguar C13S | 0.3 |
| Mono/di oleyl phosphate ester (Briphos 03D) | 1.5 |
| Silicone emulsion of Example 3 | 4.0 |
| Genapol TS | 2.5 |
| Preservative, Colour, Perfume | qs |
| Water | to 100 |

This is prepared by mixing the SLES 2EO, CDE, Briphos and Jaguar with the process water and then heating to 50° C. The Genapol is melted (50° C.) and mixed with the hot surfactant mixture which is then cooled. The silicone emulsion, perfume colour and preservative are added when the mixture is cool (less than 40° C.) using a paddle stirrer.

We claim:
1. An aqueous shampoo composition comprising, in addition to water
   (a) from 2 to 40% by weight of surfactant selected from the group consisting of anionic, nonionic, amphoteric and mixtures of surfactants thereof;
   (b) from 0.01 to 10% by weight of insoluble, non-volatile silicone which is selected from the group consisting of polyalkyl siloxanes, polyalkylaryl siloxanes and mixtures thereof;
   (c) from 0.5 to 5% by weight of suspending agent selected from the group consisting of polyethylene glycol mono- and di-esters of $C_{16-22}$ fatty acid, having from 2 to 7 ethylene oxide groups.

2. A shampoo composition as claimed in claim 1 wherein the anionic surfactant is selected from the group consisting of sodium lauryl ether sulphate 2EO, sodium lauryl ether sulphate 3EO, ammonium lauryl sulphate, ammonium lauryl ether sulphate 1EO, ammonium lauryl ether sulphate 2EO, ammonium lauryl ether sulphate 3EO or mixtures thereof.

3. A shampoo composition as claimed in claim 1 wherein the amphoteric surfactant is selected from $C_{8-18}$ alkyl amidopropyl betaine or $C_{8-18}$ alkyl betaine.

4. A shampoo composition as claimed in claim 3 wherein the amphoteric surfactant is cocobetaine.

5. A shampoo composition as claimed in claim 1 wherein the insoluble, non-volatile silicone is polydimethyl siloxane or polymethylphenyl siloxane.

6. A shampoo composition as claimed in claim 1 wherein the suspending agent is selected from the group consisting of polyethylene glycol distearate having 3 ethylene oxide groups, polyethylene glycol dipalmitate having 3 ethylene oxide groups and polyethylene glycol dioleate having 4 ethylene oxide groups.

7. A shampoo composition as claimed in claim 1 which additionally comprises a cationic conditioning agent.

8. A shampoo composition as claimed in claim 7 wherein the cationic conditioning agent is present in an amount of from 0.1 to 5% by weight.

9. A shampoo composition as claimed in claim 8 wherein the cationic conditioning agent is selected from cationic cellulose derivatives or cationic guar gum derivatives.

10. A shampoo composition as claimed in claim 9 wherein the cationic guar gum derivative is guar hydroxypropyltrimonium chloride.

* * * * *